US006737243B1

(12) United States Patent
Ise et al.

(10) Patent No.: US 6,737,243 B1
(45) Date of Patent: May 18, 2004

(54) DETERMINATION OF THE HYDROPHOBIC PULMONARY SURFACTANT PROTEIN SP-C

(75) Inventors: Wolfgang Ise, Konstanz (DE); Wolfram Steinhilber, Stockach (DE); Andreas Günther, Pohlheim-Watzenborn (DE); Reinhold Schmidt, Buseck (DE)

(73) Assignee: Altana Pharma AG, Konstanz (DE)

( * ) Notice: Subject to any disclaimer, the term of this patent is extended or adjusted under 35 U.S.C. 154(b) by 0 days.

(21) Appl. No.: 09/720,830

(22) PCT Filed: Jul. 8, 1999

(86) PCT No.: PCT/EP99/04796

§ 371 (c)(1),
(2), (4) Date: Feb. 21, 2001

(87) PCT Pub. No.: WO00/05585

PCT Pub. Date: Feb. 3, 2000

(30) Foreign Application Priority Data

Jul. 24, 1998 (EP) ............................. 98113872

(51) Int. Cl.⁷ .................. G01N 33/514; G01N 33/53
(52) U.S. Cl. .................. 435/7.92; 435/7.1; 435/7.8; 435/68.1; 435/172.2; 435/810; 435/723; 436/536; 436/513; 530/381.1; 530/388.15
(58) Field of Search ............... 435/7.1, 7.8, 7.92, 435/68.1, 70.2, 172.2, 810, 723; 436/536, 513; 530/388.1, 388.15

(56) References Cited

U.S. PATENT DOCUMENTS

| 4,656,253 A | 4/1987 | Lewicki ............... 530/387 |
| 5,156,950 A | 10/1992 | Akino et al. ............ 435/7.51 |
| 6,219,575 B1 | 4/2001 | Nemati ................ 604/20 |

FOREIGN PATENT DOCUMENTS

| EP | 0 224 590 | 6/1987 |
| EP | 0 328 679 | 8/1989 |
| EP | 0 329 794 | 8/1989 |
| WO | 89/04326 | 5/1989 |
| WO | 91/00871 | 1/1991 |
| WO | 91/18015 | 11/1991 |
| WO | 93/21225 | 10/1993 |

OTHER PUBLICATIONS

Michael Beers Inhibition of Cellular Processing of Surfactant Protein C by Drugs Affecting Intracellular pH Gradients. JBC (1996) 271: 14361–14370.*

Bligh et al.; A Rapid Method of Total Lipid Extraction and Purification; Canadian Journal of Biochemistry and Physiology; vol. 37, Aug. 1959, No. 8; pp. 911–917.

Curstedt et al.; Two Hydrophobic Low–Molecular–Mass Protein Fractions of Pulmonary Surfactant; Eur. J. Biochem; 168, 255–262 (1987).

Folch et al.; A Simple Method for the Isolation and Purification of Total Lipids from Animal Tissues; The Journal of Biological Chemistry; vol. 226, 1957; pp. 497–509.

Krämer et al.; Elisa Technique for Quantification of Surfactant Protein B (SP–B) in Bronchoalveolar Lavage Fluid; Am J Respir Crit Care Med, vol. 152, 1995; pp. 1540–1544.

Cosmi, E.V. et al, "Respiratory Distress Syndrome: Requirements of Perinatal Diagnosis, Prevention and Treatment", Surfactant Replacement Therapy in Neonatal and Adult Respiratory Distress Syndrome, ed. Lachmann B; Springer Verlag, 1988.

Dilger, I. et al, "Determination of the Pulmonary Surfactant–Associated Protein SP–B in Amniotic Fluid with a Competition ELISA", Gynecol Obstet Invest, 1994, 38:24–27.

Greene, K.E. et al, "Serial Changes in Surfactant–associated Proteins in Lung and Serum before and after Onset of ARDS", Am J Respir Crit Care Med, 1999, 160:1843–1850.

Günther, A. et al, "Surfactant Alterations in Severe Pneumonia, Acute Respiratory Distress Syndrome, and Cardiogenic Lung Edema", Am J Respir Crit Care Med, 1996, 153:176–184.

Johansson, J. et al, "Hydrophobic Surfactant Proteins SP–B and SP–C: Special Analytical Problems", Methods in Protein Sequence Analysis, eds. Jörnvall/Höög/Gustavsson; Birkhäuser Verlag Basel, 1991.

Lewis, J.F. et al, "Surfactant and the Adult Respiratory Distress Syndrome", Am Rev Respir Dis, 1993, 147:218–233.

Pryhuber, G.S. et al, "Ontogeny of Surfactant Proteins A and B in Human Amniotic Fluid as Indices of Fetal Lung Maturity", Pediatric Research, 1991, 30:597–605.

Qanbar, R. et al, "A Quantitative Method for Detecting Surfactant–Associated Protein C in Pulmonary Surfactant", Analytical Biochemistry, 1994, 216:262–270.

Seeger, W. et al, "Alveolar surfactant and adult respiratory distress syndrome", Clin Investig, 1993, 71:177–190.

Shimizu, H. et al, "Appearance of surfactant proteins, SP–A and SP–B, in developing rat lung and the effects of in vivo dexamethasone treatment", Biochemica et biophysica acta, 1991, 1081:53–60.

Possmayer; Pulmonary Perspective; A Proposed Nomenclature for Pulmonary Surfactant–Associated Proteins; Am Rev Respir Dis; 1988; 138:990–998.

van Eijk et al.; Quantitative Analysis of Pulmonary Surfactant Proteins B and C; Analytical Biochemistry 232, 231–237 (1995).

(List continued on next page.)

Primary Examiner—Long V. Le
Assistant Examiner—Changhwa J. Cheu
(74) Attorney, Agent, or Firm—Jacobson Holman PLLC

(57) ABSTRACT

Methods for determining the strongly hydrophobic pulmonary surfactant protein SP-C, SP-C specific antibody and a reagent kit for carrying out the methods are described.

11 Claims, No Drawings

OTHER PUBLICATIONS

Wei et al.; Production of Human Surfactant Protein C in Milk of Transgenic Mice; Transgenic Research 4, 232–240 (1995).

Beers et al.; Localization, Synthesis, and Processing of Surfactant Protein SP–C in Rat Lung Analyzed by Epitope–Specific Antipeptide Antibodies; The Journal of Biochemistry; vol. 269, No. 32; 1994; pp. 20318–20328.

Beers et al.; Rapid Communication, an Antibody with Specificity for Surfactant Protein C Precursors; Identification of Pro–SP–C in Rat Lung; Am. J. Respir. Cell Mol. Biol., vol. 7, pp. 368–378; 1992.

* cited by examiner

DETERMINATION OF THE HYDROPHOBIC PULMONARY SURFACTANT PROTEIN SP-C

TECHNICAL FIELD

The invention relates to methods for determining the pulmonary surfactant protein SP-C, to SP-C-specific antibodies and to the provision of a reagent kit for carrying out the methods.

PRIOR ART

The lungs of all vertebrates contain a substance mixture called "pulmonary surfactant". It has surface-active properties and reduces surface tension in the alveolar region of the lungs. In addition to phos-pholipids such as dipalmitoylphosphatidylcholine (DPPC) and phosphatidylglycerol (PG), the pulmonary surfactant contains proteins as further essential components. To date, four different surfactant proteins have been described, which are designated SP-A, SP-B, SP-C and SP-D, corresponding to the order in which they were discovered (Possmayer, F., A Proposed Nomenclature for Pulmonary Surfactant-associated Proteins. Am. Rev. Respir. Dis. 1988, 138, 990–998). The term SP stands for surfactant protein (surfactant-associated protein, SP).

SP-B and in particular SP-C are strongly hydrophobic proteins. The total proportion of hydrophobic proteins in the pulmonary surfactant is approximately 1% (Curstedt, T., J örnvall, H., Robertson, B., Bergmann, T., Bergren, P.: Two Hydrophobic Low-Molecular-Mass Protein Fractions of Pulmonary Surfactant. Characterization and Biophysical Activity. Eur. J. Biochem. 1987, 168, 255–262).

The determination (detection and in particular quantification) of these hydrophobic proteins in samples of pulmonary surfactant (for example from lung lavage) frequently gives unsatisfactory results when the techniques employed for hydrophilic proteins are used, if it is possible at all. The methods which are customarily used for separating and determining hydrophilic proteins, such as, for example, "Western blotting" or ELISA (Enzyme-Linked Immunosorbent Assay) techniques can be applied to hydrophobic proteins only under certain conditions, since on the one hand the "Western blot" per se is semiquantitative and, on the other hand, the use of an ELISA is very problematic, since it can generally only be carried out with proteins which are soluble in aqueous systems. In most cases, only traces of the analytes to be quantified are present. Furthermore, in the samples to be analyzed, SP-B and SP-C are frequently associated with other hydrophobic substances (for example lipids), which renders quantification by customary methods even more difficult. In the ELISA, the substance to be examined is usually not separated prior to the determination from the other components which are contained in the mixture. Van Eijk and co-workers (Van Eijk, M., De Haas, C. G. M. and Haagsman, H. P.: Quantitative Analysis of Pulmonary Surfactant Proteins B and C. Analytical Biochemistry 1995, 232, 231–237) describe a process for quantifying SP-C and SP-B in samples of pulmonary surfactant. Extracts containing surfactant proteins are separated by high-pressure liquid chromatography, and SP-B or SP-C are detected and quantified by absorption at 228 nm. (The detection limits are at 1 µg of SP-B and 4 µg of SP-C.)

For SP-B, a quantitative detection by ELISA technique is described (Krämer, H. J., Schmidt, R., Günther, A., Becher, G., Suzuki, Y., Seeger, W.: ELISA Technique for Quantification of Surfactant Protein B (SP-B) in Bronchoalveolar Lavage Fluid. Am. J. Respir. Crit. Care Med. 1995, 152, 1540–1544). An immunoassay for the determination of SP-C has hitherto not been described, apparently because the preparation of SP-C-specific antibodies has not been successful (Beers, M. F., Wali, A., Eckenhoff, M. F., Feinstein, S. I., Fisher, J. H. and Fisher, A. B.: Am. J. Respir. Cell Mol. Biol. 1992, 7, 368–378).

DESCRIPTION OF THE INVENTION

It is an object of the invention to provide processes permitting the determination of pulmonary surfactant protein SP-C in a sample in a simple manner and with high sensitivity.

Surprisingly, we have succeeded in providing antibodies which are specific for SP-C, and thus allow SP-C to be determined by an immunological method.

Accordingly, the invention provides processes for determining SP-C in a sample, where the determination is carried out by an immunological method.

Further subject matters follow from the subclaims.

In the context of the invention, the determination of SP-C is to be understood as the detection and, in particular, the quantification of SP-C.

In the context of the invention, the term "SP-C" is to be understood, in analogy to the nomenclature proposed by Possmayer (Possmayer, F.: A Proposed Nomenclature for Pulmonary Surfactant-associated Proteins. Am. Rev. Respir. Dis. 1988, 138, 990–998), as the "family" of surfactant proteins which is present in natural pulmonary surfactant or the amnionic fluid of mammals designated SP-C.

Furthermore, the term "SP-C" also includes chemically synthesized or recombinantly prepared SP-C and modifications of SP-C, for example those modifications where one or more amino acids are missing or have been replaced by other amino acids. Chemically synthesized or recombinantly prepared SP-C and modifications of SP-C are described, for example, in WO91/18015, WO91/00871, WO89/04326, WO93/21225 and also in WO95/32992.

SP-C is preferably understood as meaning the surfactant protein SP-C which is present in human pulmonary surfactant or in human amnionic fluid.

In the context of the present invention, "immunological methods" are understood as meaning analytical methods based on immunochemistry, in particular on an antigen-antibody reaction. Examples of immunological methods include immunoassays such as radioimmunoassay (RIA), enzyme immunoassay (EIA, combined with solid-phase technique: ELISA) or else immunofluorescence assays. The immunoassay is carried out by exposing the sample to be investigated to an SP-C-binding antibody and detecting and quantifying the amount of antibody which binds to SP-C. In these assays, detection and quantification is carried out directly or indirectly in a known manner. Thus, detection and quantification of the antigen-antibody complexes is made possible by using suitable labels which may be carried by the antibody directed against SP-C and/or by a secondary antibody directed against the primary antibody. Depending on the type of the abovementioned immunoassays, the labels are, for example, radioactive labels, fluorescent dyes or else enzymes, such as phosphatase or peroxidase, which can be detected and quantified with the aid of a suitable substrate.

In one embodiment of the invention, the immunological method is carried out with the aid of a suitable solid phase. Suitable solid phases which may be mentioned include the customary commercial microtiter plates made of polystyrene or membranes (for example made of polyvinylidene difluoride, PVDF) which are customarily used for the ELISA technique. Surprisingly, it has been found that even chromatography plates are suitable for use as solid phase in the process according to the invention. The implementation of the process according to the invention using chromatography plates is hereinbelow also referred to as immuno-TLC.

To carry out the process according to the invention, the sample is applied to the solid phase. The sample is preferably a solution of SP-C in a suitable solvent, and the solvent is evaporated after the sample has been applied to the solid phase. To prepare a solution of the sample to be investigated in a suitable solvent, it is advantageous to use organic solvents or solvent mixtures which have proved to be suitable for solubilizing hydrophobic proteins. Examples which may be mentioned are short-chain alcohols, in particular methanol, ethanol, 2-propanol (isopropanol) or n-propanol. Furthermore, in connection with immuno-TLC, mixtures of non-polar and polar solvents were found to be useful, suitable non-polar solvents being, in particular, chloroform, methylene chloride and toluene, and suitable polar solvents being short-chain alcohols. Chloroform/methanol mixtures may be mentioned as being particularly preferred.

If desired, small amounts of water and/or acid or base may be added to the abovementioned solvents or solvent mixtures to improve the solvent properties.

If the SP-C content of a bronchoalveolar lavage (BAL) sample or a sample of amnionic fluid is to be determined with the aid of immuno-TLC, it is advantageous to transfer the SP-C prior to application to the solid phase from the aqueous phase (BAL sample, amnionic fluid) to a suitable organic solvent or solvent mixture. This is expediently carried out by extraction with suitable organic solvents or solvent mixtures, for example by the extraction method of Bligh-Dyer (Can. J. Biochem. Physiol. 1959, 37, 911–917) and subsequent Folch washing (J. Biol. Chem. 1957, 226, 497–509).

If the SP-C content of a bronchoalveolar lavage (BAL) sample or a sample of amnionic fluid is to be determined with the aid of the ELISA technique, it is advantageous to dilute the sample with a suitable water-miscible solvent or solvent mixture. Suitable water-miscible solvents or solvent mixtures which may be mentioned are, in particular, short-chain alcohols, such as ethanol and isopropanol, or mixtures thereof.

Moreover, it has been found to be expedient for the method according to the invention to separate or remove interfering components in the sample to be investigated on the solid phase prior to the immunological detection of SP-C in the sample. This is particularly advantageous in cases where in the samples to be investigated other components, such as other surfactant proteins or else lipids, are present in addition to SP-C.

If chromatography plates are used as the solid phase in the method according to the invention, the sample can be separated by thin-layer chromatography. To this end, the sample is, after application and evaporation of the solvent, subjected to thin-layer chromatography. Suitable chromatography plates are all plates whose coating is suitable for separating hydrophobic mixtures in organic media. The HPTLC plates sold by Merck Darmstadt under the trade name Diol, which have a modified silica matrix, have been found to be particularly suitable in this context. Suitable solvents for the thin-layer chromatography of hydrophobic proteins are organic solvents and solvent mixtures. Particularly expedient is the use of mixtures of non-polar and polar solvents, suitable non-polar solvents being, in particular, chloroform, methylene chloride and toluene, and suitable polar solvents being short-chain alcohols, in particular methanol, ethanol and isopropanol. If desired, it is possible to add small amounts of water and/or acid or base. Preference is given to mixtures of chloroform and methanol to which small amounts of water and ammonia are added. The application of the samples to the plates and the practice of the separation are carried out in a customary manner, for example by means of customary commercial apparatuses. The sample to be applied is preferably a solution of SP-C in an organic solvent. In preparation for the immunological detection, the chromatography plates are dried after the separation by thin-layer chromatography.

It has surprisingly been found that, if the solid phase used is a polystyrene microtiter plate customarily used in the ELISA technique, interfering components in the sample can be removed after the application of the samples by one or more selective washing steps. To this end, BAL samples to be investigated are expediently diluted prior to application with a water-soluble organic solvent (for example an alcohol such as isopropanol) and adjusted to a pH below 7 (preferably pH 3–4). If desired, variable adsorption of the SP-C on the surface of the plate caused by inhomogeneities of the biological samples can be minimized. This can be effected, for example, after the application and the drying of the sample—and before a washing—by re-dissolution in a suitable solvent, such as, for example, trifluoroethanol, followed by a drying step. Interfering components can be removed, after application of the samples and evaporation of the solvent, by washing with suitable solvents. Thus, interfering lipids, for example, can be removed by one or more washings with methanol.

In preparation for the immunological detection, the solid phase, if desired, is pretreated in a suitable manner. Unspecific binding sites on the solid phase, for example, can be saturated using a suitable blocking solution, such as gelatin, or a protein solution. The solid phase is subsequently incubated with a solution of the SP-C-specific antibody. If this antibody is not labeled, detection and quantification can be carried out with the aid of a labeled secondary antibody which recognizes the primary antibody. To this end, excess primary antibody is removed by washing and the plate is then incubated with a labeled secondary antibody. After removal of excess antibody by washing, detection and quantification of the antigen-antibody complexes is carried out with the aid of the label.

Labels which are suitable for the detection and quantification step and which can be carried by the primary or secondary antibody are known to the person skilled in the art. Examples which may be mentioned include radioactive labels, fluorescent dyes and, preferably, enzymes such as phosphatase or peroxidase, which permit calorimetric or chemoluminescent detection. Depending on the label used, the subsequent detection or quantification is carried out in a known manner.

When carrying out the method according to the invention with the aid of the ELISA technique, the antigen-antibody complexes are preferably detected and quantified via an enzyme-catalyzed color reaction using a peroxidase-conjugated antibody and ABTS (2,2'-azino-di[3-ethylbenzothiazolinesulfonate]) as substrate. However, it is also possible to use other chromogenic, chemoluminescent or fluorogenic methods known to the person skilled in the art for the detection.

When carrying out the method according to the invention with the aid of immuno-TLC, the antigen-antibody complexes are preferably detected and quantified via an enzyme-catalyzed chemoluminescence reaction using Luminol® as substrate. However, it is also possible to use other chromogenic, chemiluminescent or fluorogenic methods known to the person skilled in the art for the detection.

As already mentioned, we have surprisingly succeeded in providing antibodies which are specific for SP-C, in particular for the SP-C which is present in human pulmonary surfactant or amnionic fluid. The invention therefore also provides an antibody which is specific for SP-C, in particular specific for SP-C which is present in human pulmonary surfactant or amnionic fluid. The antibody is furthermore advantageously characterized by the fact that it does not show any cross reactivity with other surfactant proteins such as SP-A and SP-B.

The SP-C-specific antibodies are preferably polyclonal antibodies.

The SP-C-specific antibodies are prepared analogously to processes known to the person skilled in the art (as described, for example, in Antibodies: A Laboratory Manual. Eds. E. Hariow and D. Lane. Cold Spring Harbor Laboratory 1987).

The preparation of polyconal antibodies directed against SP-C is expediently carried out by known immunization methods. Here, it has been found to be advantageous to use recombinant SP-C (herein-below also referred to as rSP-C) as antigen in the immunization process, and to employ larger amounts of antigen than are usually used, and to increase the number of antigen administrations. In the immunization process, between 0.5 mg and 2 mg (preferably 1 mg) of rSP-C are expediently employed per administration of antigen, where the number of antigen administrations is advantageously between 5 and 7, preferably at an interval of from three to six weeks (preferably four weeks). Furthermore, it has been found to be advantageous to use the rSP-C in the form of insoluble particles (aggregates or precipitates), or coupled to a carrier molecule (for example protein or beads). Aggregates and precipitates can be obtained in a customary manner, expediently as described in the "Examples" section.

Suitable rSP-C for use in the immunization process which may be mentioned includes recombinant human-identical dipalmitoylated SP-C (rhSP-C2Pam) or recombinant modifications of SP-C. Recombinant modifications of SP-C which may be mentioned include, for example, non-palmitoylated human-identical SP-C (rhSP-C) or the SP-C modification with 34 amino acids described in the international patent application WO95/32992, where the amino acids in positions 4 and 5 of the amino acid sequence are phenylalanine and the amino acid in position 32 of the amino acid sequence is isoleucine (the stated positions within the amino acid sequence are based on the amino acid sequence for the peptides of the formula I described in WO95l32992). The preparation of this peptide, which is designated rSP-C34 (FF/1), by genetic engineering is likewise described in WO95/32992.

The invention therefore also relates to a process for preparing polyclonal antibodies directed against SP-C by immunization, in particular against human SP-C, where the antigen component used for the immunization is recombinant SP-C. By way of example, the preparation of antibodies which are specific for SP-C, and an immunological determination of SP-C in a sample, are described below.

EXAMPLES

1. Preparation of Polyclonal Antibodies
1.1 Preparation of Antisera Against rSP-C 1 mg of rSP-C [rhSP-C2 Pam, rhSP-C or rSP-C34(FF/I)], dissolved in isopropanol/water (95:5), pH 4, was evaporated in a vacuum concentrator (Speedvac®) and resuspended in 0.5 ml of phosphate-buffered saline (PBS) by incubation with ultrasound (5 minutes) in an ultrasonic bath. This process gives aggregated rSP-C, which was used as antigen. The suspension was then mixed with 0.2 ml of Freund's adjuvant complete for the basic immunization and with 0.5 ml of Freund's adjuvant incomplete for the booster injections. To achieve this, the solution was pushed back and forth 5–10× between two syringes linked by a canula. 0.2 ml portions of the emulsion were then injected subcutaneously into rabbits. The immunization scheme followed standard protocols: after the primary immunization, 5 booster injections were adminstered at intervals of 4 weeks. Blood samples were taken in each case 10 days after the last injection to monitor the development of the titer. As soon as the titer was satisfactory, 50 ml of blood were taken and serum was prepared by standard methods.

It is also possible to use ABM-S (Antibody Multiplier Special) for the basic immunization and AMB-N (Antibody Multiplier Normal) for the booster injections, or to use other known adjuvants, for the immunization. The use of Freund's adjuvant results, on the one hand, in a considerably higher antibody titer than when ABM adjuvant is used, on the other hand, Freund's adjuvant induces an immune response in 100% of the animals, and when ABM is used, this is the case in only about 50% of the animals. Furthermore, the rSP-C can be coupled to a suitable carrier material, such as, for example, activated CH Sepharose, and then be administered subcutaneously to the rabbits, with or without adjuvant, preferably with Freund's adjuvant.

All suitable animal species can be employed for preparing antibodies. Thus, in addition to rabbits, it is also possible to use chickens.

1.2 Determination of the Titer

In the individual sera, the titer was determined at different dilutions using Western blot analysis by standard methods. For gel electrophoresis, the SDS/tricine method by Schägger and Jagow (Analyt. Biochem. 1987, 166:368–379) was used. Here, 0.1 μg of the appropriate rSP-C were separated in a 15% strength polyacrylamide gel, transferred to PVDF (polyvinylidene difluoride) membranes and incubated with the sera at dilutions of 1:1,000, 1:5,000, 1:10,000 and 1:25,000, 1:50,000, 1:100,000 and 1:200,000. Bound primary antibodies were detected by peroxidase-coupled secondary antibodies (anti-rabbit IgG or anti-chicken IgY) via chemoluminescence using the ECL (Enhanced Chemiluminescence) system from Amersham (Brunswick). The titers varied from 1:10,000 to >1:200,000. The detection limits in the Western blot varied from <10 to 100 ng.

1.3 Specificity of the Antibodies Obtained: Cross Reactions With Other Pulmonary Surfactant Proteins All antisera/antibodies reacted with the rSP-C employed in each case as antigen. Surprisingly, they cross reacted with natural dipalmitoylated SP-C (hSP-C2 Pam; isolated from human or animal lung lavage), and also with other natural or modified rSP-Cs.

The antisera/antibodies do not react with other pulmonary surfactant proteins such as SP-A or SP-B. The antisera are therefore suitable for detecting SP-C, in particular human SP-C, in solutions having an unknown content of SP-C, such as lung lavage or amnionic fluid, or for carrying out the detection on tissue sections using immunohistochemistry and immunocytochemistry.

2. Immuno-TLC

2.1 Sample Preparation: Extraction of SP-C From Bronchoalveolar Lavages (BAL)

0.8 ml of BAL, 2.0 ml of methanol and 1.0 ml of chloroform are pipetted into a centrifuge tube and thoroughly mixed using a vortex. Addition of another 1.0 ml of chloroform results in phase separation. After renewed mixing, 1.0 ml of ultrapure water are added, and the samples are once more mixed with the vortex for approximately 30 seconds. The samples are centrifuged at 2400 rpm for 5 minutes. The bottom phases are (if necessary in two steps) transferred into Eppendorf caps and evaporated to dryness using the Speed-Vac combination. In the meantime, the top phases are washed with 2.0 ml of chloroform/methanol/water (86/14/1 by volume). The second bottom phases are in each case transferred into the same Eppendorf caps of the first phase, centrifuged as above and also evaporated to dryness. The top phases are discarded. The extracts are taken up in chloroform/methanol 70:30 (v/v).

2.2 Thin-layer Chromatography (TLC)

For thin-layer chromatography, HPTLC plates having a modified silica matrix, as sold by Merck Darmstadt under the trade name Diol, were used. The samples were applied automatically onto the HPTLC plates using a Lingomat IV (Camag, Berlin). After the samples had been applied, the plates were air-dried and chromatographed using a $CHCl_3$:MeOH mixture [$CHCl_3$/MeOH/25% strength $NH_4OH/H_2O$=32.5/15/1/2 (by volume)] as liquid phase. After the chromatography, the plates were dried.

2.3 Immunological Detection and Quantification

To saturate non-specific binding sites, the dried HPTLC plates were incubated for 4 hours with 3% strength fish gelatin in PBS which contained 150 mM NaCl, 12 mM $Na_2HPO_4$ and 3 mM $NaH_2PO_4$ (ph 7.4). The plates were then incubated overnight and, in the presence of the primary SP-C-specific antibody, shaken gently, usually at a dilution of 1:10,000. Unbound antibodies were removed by repeated washing with TBS/T from 4 mM tris-HCl, 100 mM NaCl, 0.05% Tween-20 (pH 7.4). For hybridization with the primary antibody, the plates were incubated for 2 hours with horseradish peroxidase-conjugated secondary antibody, at a dilution of 1:100,000 in TBS/T. Unbound antibodies were removed as described above by repeated washing of the plates with TBS/T. Immunoreactive complexes were visualized using ECL detection systems (consisting of Luminol® and enhancer) from Amersham Buchler. The plates were exposed to an X-ray film (Hyperfilm Amersham) for 1–10 minutes.

2.4 Video-imaging of the X-ray Films and Evaluation by Computer

To quantify the immunocomplexes, the X-ray films were digitalized using a Video-Imager (Cybertech, Berlin, Germany). The signal intensities on the X-ray films were evaluated with the aid of a computer using the densitometer software Diana (Raytest).

2.5 Quantification of SP-C

To determine pulmonary surfactant protein SP-C, BAL fractions were extracted. In order to quantify the small amounts of SP-C, it is necessary to separate the target protein from the large proportion of lipids. This is achieved by thin-layer chromatography. The SP-C in the fractions applied is quantified with the aid of standards.

3. ELISA Technique

3.1.1 Sample Preparation and Coating of the Microtiter Plates Using PBS Buffer The carrier material used for the ELISA were microtiter plates with 96 wells made of polystyrene (Polysorp® F96) with certificate, Nunc, Wiesbaden). The standard (human-identical rSP-C, c=300 µg/ml) was diluted with isopropanol/water (80:20, pH 3.0) in a series of concentrations from 40 ng/well to 312.5 pg/well (v=100 µl/well, corresponding to c=0.4–0.003125 µg/ml of rSP-C). The samples to be measured (bronchoalveolar lavages, BAL) were diluted with isopropanol/water (80.20, pH 3.0). Usually, 10 µl or 20 µl of BAL in a total volume of 100 µl were pipetted into the wells. Each plate also carried an internal standard (BAL with a defined concentration of SP-C). All samples and standards were measured in duplicate. All dilutions were carried out in 2 ml reaction vessels made of polypropylene (Eppendorf, Hamburg).

After the pipetting of the samples and standards, the microtiter plates were incubated in a ventilated drying cabinet at 37° C. for 6 hours to dryness. The variable adsorption of SP-C at the surface of the plates, which is caused by inhomogeneities of the biological samples, was minimized by re-uptake in 100 µl of trifluoroethanol. After a further drying step (37° C., 3 hours), the phospholipids, which were present in about 50–100-fold excess relative to SP-C, were selectively removed by two successive washing steps. In the first step, 200 µl of methanol were added and the plate was incubated at room temperature with shaking (20 minutes). The solvents were decanted off, and the plates were then washed once more with 200 µl of methanol, and the methanol was immediately decanted off. The plates were then washed three times with 200 µl of PBS/0.5% Tween 20.

3.1.2 Sample Preparation and Coating of the Microtiter Plates Using Tris/Cl Buffer All standard solutions and aqueous samples of SP-C were mixed with 80% 2-propanol/20% water (v/v) pH 3.5. SP-C standards (human rSP-C, c=300 µg/ml) were diluted to final concentrations of 0.4–0.003125 µg/ml. Aqueous samples (bronchoalveolar lavage fluids, BALF) were mixed 1:5 (v/v) with 80% 2-propanol/20% water (v/v) pH 3.5. All dilutions were performed in 20 ml polypropylene vials (Eppendorf, Hamburg, Germany) in order to avoid adsorption of SP-C to the vessel wall, before a volume of 100 µl of each sample or standard was transferred to polystyrole microtiter plates (Polysorp® F96, with certificate, Nunc, Wiesbaden, Germany). BALF samples with known SP-C content were coprocessed on each microtiter plate. All standards and samples were processed in duplicate.

Fluid removal was achieved by overnight evaporation at 37° C. The subsequent addition of 100 µl/well 1,1,1-trifluoroethanol, again followed by evaporation at 37° C. (3 h), optimized adsorption of the biological samples to the plate. Phospholipids were selectively removed by two subsequent washing procedures with methanol. For this purpose, 200 µl/well methanol was applied to the plates and incubated for 20 min at ambient temperature with gentle shaking. Following decantation of the organic solvent, this step was repeated without further incubation. Immediately after decantation, wells were washed three times with 50 mM Tris/Cl pH 7.6+0.5% Tween 20 (Sigma, Deisenhofen, Germany).

3.2.1 Immunological Detection and Quantification Using PBS Buffer

The ELISA system described below is based on the method developed by Reinke et al. (Prostaglandins 1989, 37:577–586). To block excess binding sites, the sample was incubated for 2 hours with PBS/1% bovine serum albumin (BSA). After rinsing three times with PBS/0.5% Tween 20, the SP-C antiserum was applied. To this end, the antiserum was diluted 1:2,000 in PBS/1% BSA, 200 µl of this solution were pipetted into each well, and the plate was incubated at room temperature for 12–15 hours and subsequently once more washed three times (see above). 200 µl of a 1:1000 dilution of biotinylated anti-rabbit antibody (donkey, Amersham-Buchler, Brunswick) in PBS/1% BSA were then applied, and the plate was incubated at room temperature for 2 hours. To remove excess antibody, the plate was washed three times. The sensitivity of the test was then enhanced using the avidine/biotin peroxidase technique (AB-Komplex, Dako, Hamburg). To this end, a drop of avidine solution and a drop of biotinylated horseradish peroxidase solution were added to 5 ml of PBS, and the mixture was equilibrated for 30 minutes. 200 µl of a 1:50 dilution of this stock solution in PBSI1% BSA were incubated on the plates for 2 hours, and the plates were subsequently once more washed three times (see above).

The enzymatic color development was initiated by addition of the substrate 2,2'-azino-di-[3-ethylbenzothiazolinesulfonate] (ABTS) [NGO, T. T.: Chromogenic substrates for enzyme immunoassay in nonisotopic immunoassay. New York: Plenum Publishing Corporation, 1988, p. 57–84]. To this end, 20 mg of ABTS and 10 µl of 30% $H_2O_2$ were dissolved in 30 ml of substrate buffer (60 mM sodium acetate trihydrate, 50 mM sodium dihydrogen phosphate monohydrate pH 4.2) [PETERS, H. J.; BAUMGARTEN, H.; SCHULZE, M.: Monoklonale Antikörper-Herstellung und Charakterisierung. Berlin: Springer Verlag, 1985], and 200 µl of this solution were pipetted into the wells. After color development (2 hours, room temperature or overnight at 4° C.), the samples were evaluated spectrophotometrically at 405 or 450 nm in an ELISA photometer (Reader 400 V. 1.1, SLT, Crailsheim).

3.2.2 Immunological Detection and Quantification Using Tris/Cl Buffer

Nonspecific protein binding to wells was blocked with 200 µl 50 mM Tris/Cl pH 7.6 buffer containing 1% (w/v) bovine serum albumin (BSA, Paesel and Lorei, Frankfurt/Main, Germany). After 2 h incubation at ambient temperature, wells were washed three times with 50 mM Tris/Cl pH 7.6+0.5% Tween 20 and a 1:2,000 dilution (v/v) of anti-SP-C antiserum in 50 mM Tris/Cl pH 7.6+1% BSA was added. After 12–15 h incubation at ambient temperature, wells were washed extensively as described above and incubated for 2 h with 200 µl of biotinylated anti-rabbit antibody (Amersham Buchler, Braunschweig, Germany; 1:1,000 in 50 mM Tris/Cl pH 7.6+1% BSA). After removal of free antibody, incubation with 200 µl of avidin-biotin-horseradish peroxidase complex (ABComplex, Dako, Glostrup, Denmark; stock solution according to the specification of the supplier, working solution 1:50 in 50 mM Tris/Cl pH 7.6+1% BSA) was performed for another 2 h with subsequent washing. Enzymatic dye conversion was initiated by charging the wells with 200 µl 2,2'-azino-di-[3-ethylbenzthiazolinsulfonate] (ABTS, Boehringer, Mannheim, Germany; 20 mg in 30 ml substrate buffer (60 mM sodium acetate+50 mM $NaH_2PO_4$ pH 4.2)+10 µl 30% $H_2O_2$). After overnight incubation at 4° C., absorbance was measured at 450 nm.

3.3 Quantification of SP-C

The SP-C in the BAL samples was quantified by constructing a standard curve by computer-supported cubic-spline interpolations using rSP-C standards which had been carried along.

Commercial Utility

The present method according to the invention allows the quantitative determination of the SP-C content of a sample in an advantageous manner. For example, it is possible to determine the SP-C content in human pulmonary surfactant or amnionic fluid, or else to detect SP-C in tissue sections by immunohistochemistry and immunocytochemistry. The method according to the invention can thus be employed advantageously for diagnosing disease conditions associated with a pulmonary surfactant deficit or a change in the composition of pulmonary surfactant (Günther et al.: Surfactant Alterations in Severe Pneumonia, Acute Respiratory Distress Syndrome and Cardiogenic Lung Edema. Am. J. Respir. Crit. Care Med. 1996, 153, 176–184; Seeger et al.: Alveolar Surfactant and Adult Respiratory Distress Syndrome. Clin. Investig. 1993, 71, 177–190; Cosmi et al.: Respiratory Distress Syndrome: Requirements of Perinatal Diagnosis, Prevention and Treatment. In Lachmann B. Ed.: Surfactant Replacement Therapy in Neonatal and Adult Respiratory Distress Syndrome, Springer Verlag 1988). Disease conditions which may be mentioned as examples are Infant Respiratory Distress Syndrome (IRDS) or Adult Respiratory Distress Syndrome (ARDS).

The invention also provides a method for diagnosing IRDS or ARDS which comprises determining the SP-C content in human pulmonary surfactant or in amnionic fluid by an immunological method.

The invention also relates to a reagent kit for carrying out the method according to the invention, wherein the reagent kit comprises an SP-C-specific antibody. Depending on how the method is carried out, the kit comprises other components. Other components which may be mentioned as examples are labeled secondary antibodies, buffer solutions, washing solutions, reagents which are required for the detection step, chromatography plates or microtiter plates and organic solvents or solvent mixtures.

What is claimed is:

1. An isolated polyclonal antibody which is specific for the human pulmonary surfactant protein SP-C.

2. An isolated polyclonal antibody, obtainable by an immunization process in which recombinant human surfactant protein SP-C is used as antigen component and the antibody is specific for SP-C which is present in human pulmonary surfactant.

3. A method for determining human pulmonary surfactant protein SP-C in a sample by solid phase ELISA enzyme immunoassay which comprises the steps of
   (i) providing a sample to the investigated,
   (ii) providing an antibody as claimed in claim 1,
   (iii) exposing the sample to be investigated to a solid phase and the antibody, and
   (iv) detecting and quantifying the amount of the antibody which binds to SP-C.

4. A method for determining human pulmonary surfactant protein SP-C in a sample, which comprises carrying out the determination by a solid phase ELISA enzyme immunoassay using an antibody as claimed in claim 2.

5. The method as claimed in claim 3, wherein the solid phase is a chromatography plate and the sample is separated on the chromatography plate prior to the enzyme immunoassay being carried out.

6. The method as claimed in claim 4, wherein the solid phase is a chromatography plate and the sample is separated on the chromatography plate prior to the enzyme immunoassay being carried out.

7. The method as claimed in claim 4, wherein the solid phase is a chromatography plate and the sample is separated on the chromatography plate prior to the enzyme immunoassay being carried out.

8. The method as claimed in claim 3, wherein the solid phase is a microtiter plate.

9. The method as claimed in claim 4, wherein the solid phase is a microtiter plate.

10. A method for determining human pulmonary surfactant protein SP-C in a sample, which comprises carrying out the determination by a solid phase enzyme immunoassay, wherein, in the enzyme immunoassay, the sample is exposed to a first, human pulmonary surfactant protein SP-C-binding antibody, and the amount of bound antibody is measured using a second antibody carrying an enzyme label, where the measurement is carried out by an enzyme-catalyzed colour reaction or chemiluminescence.

11. A reagent kit for carrying out a method as claimed in claim 10, wherein the kit comprises a human SP-C-specific antibody.

* * * * *